United States Patent [19]

Kastrubin et al.

[11] 4,121,593

[45] Oct. 24, 1978

[54] APPARATUS FOR CURRENT PULSES ACTION UPON CENTRAL NERVOUS SYSTEM

[76] Inventors: Eduard Mikhailovich Kastrubin, Frunzenskaya naberezhnaya, 36, kv. 105; Valentin Matveevich Nozhnikov, Krasnodarskaya ulitsa, 33, kv. 82, both of Moscow, U.S.S.R.

[21] Appl. No.: 761,254

[22] Filed: Jan. 21, 1977

[30] Foreign Application Priority Data

Jan. 21, 1976 [SU] U.S.S.R. .............................. 2307051

[51] Int. Cl.$^2$ ............................................. A61N 1/36
[52] U.S. Cl. ..................................... 128/421; 128/1 C
[58] Field of Search ............... 128/1 D, 2.1 R, 419 R, 128/420 A, 420 R, 421, 422, 423

[56] References Cited

U.S. PATENT DOCUMENTS

| | | | |
|---|---|---|---|
| 1,908,688 | 5/1933 | Call | 128/421 |
| 2,771,554 | 11/1956 | Gratzl | 128/421 |
| 2,993,178 | 7/1961 | Burger | 128/421 X |
| 3,464,416 | 9/1969 | Williams | 128/1 C |
| 3,648,708 | 3/1972 | Haeri | 128/1 C X |
| 3,791,373 | 2/1974 | Winkler et al. | 128/1 C |
| 3,989,051 | 11/1976 | Nozhnikov et al. | 128/1 C |

FOREIGN PATENT DOCUMENTS

148,150   1/1961   U.S.S.R. .................................. 128/1 C

*Primary Examiner*—William E. Kamm

*Attorney, Agent, or Firm*—Steinberg & Blake

[57] ABSTRACT

An apparatus for current pulses action upon the central nervous system, in which current pulses are supplied from a unit for rhythmic current pulse action upon the central nervous system of a patient via a unit for regulating the duration of current pulses or via an intermittent analgesia unit, a unit for adjusting the amplitude of current pulses and a unit for indicating the mean current intensity value to the patient through electrodes, a cathode attached in the patient's forehead area and an anode attached in the patient's neck area below the mastoids, the above mentioned pulses being stopped by means of a patient protection unit, when a specific amplitude of current pulses is attained. The apparatus provides for regulation of the repetition frequency of current pulses, their amplitude and the level of the additional direct component, depending on the intensity of pain in the patient. For this purpose, an autoelectroanalgesia level remote control unit is provided, which is coupled by three outputs thereof respectively to the intermittent analgesia unit, to the unit for adjusting the amplitude of current pulses, which is additionally connected to a power unit, and to the power unit. All this enables the patient, depending on the intensity of pain, to select an individual level of anesthesia. In this case, during acute pain, the intensity of pulse action is increased by simultaneous step-up of the repetition frequency of pulses, their amplitude and the level of the additional direct component.

4 Claims, 2 Drawing Figures

APPARATUS FOR CURRENT PULSES ACTION UPON CENTRAL NERVOUS SYSTEM

The present invention relates to an improvement in an apparatus for current pulses action upon the central nervous system.

This invention can be employed for autoelectroanalgesia by a patient in pain, e.g. during delivery.

There is shown in U.S. Pat. No. 3,989,051 an apparatus for current pulses action upon the central nervous system, in which current pulses are applied to a patient through electrodes, a cathode attached to the patient's forehead and an anode attached to the area of the patient's neck, below the mastoids, in order to produce in the central nervous system of the patient the second level of the first stage of general electro-anesthesia from a series circuit comprising: a unit for rhythmic current pulse action upon the central nervous system, a unit for regulating the duration of current pulses or an intermittent analgesia unit, a switch, a unit for adjusting the mean current intensity value, which permits obtaining the second level of the first stage of general electro-anesthesia without causing any side effects in the patient, said current pulses being stopped, when a specific amplitude of current pulses is reached, by means of a patient protection unit.

While the disclosed apparatus is quite suitable for electro-anesthesia administered by a physician to reduce pain in a patient, it has been established that under certain conditions the patient is able to adjust the electro-anesthesia level depending on the intensity of pain, which permits anesthesia conforming to individual peculiarities of pain reaction, increased intensity of pulse action in the period of acute pain.

It is an object of the present invention to improve the apparatus for current pulses action upon the central nervous system in order to ensure control of the level of the pulse action by a patient, depending on the appearing pain.

Another object of the present invention is to improve the apparatus for current pulses action upon the central nervous system in order to be able to intensify the pulse action during acute pain.

This is achieved in that an apparatus for current pulses action upon the central nervous system is provided, in which current pulses are applied to a patient through electrodes, a cathode attached in the patient's forehead area and an anode attached in the patient's neck area below the mastoids, in order to produce in the patient's central nervous system the second level of the first stage of general electro-anesthesia from a series circuit comprising a unit for rhythmic current pulse action upon the central nervous system, a unit for intermittent analgesia or a unit for regulating the duration of current pulses, a switch, a unit for adjusting the amplitude of current pulses and a unit for indicating the mean current intensity value, which permits obtaining the second level of the first stage of general electro-anesthesia without any side effects in the patient, said pulses being stopped, when a specific amplitude of current pulses is attained, by means of a patient protection unit, and in which, according to the invention, an autoelectroanalgesia level remote control unit is provided, which is connected, respectively, to three units, namely to the intermittent analgesia unit, to the unit for adjusting the amplitude of current pulses and to a power unit so that said remote control unit regulates at the outputs of said three units, respectively the repetition frequency of current pulses, their amplitude and the level of the additional direct, component in conformity with the intensity of patient's pain, the unit for adjusting the amplitude of current pulses being additionally coupled to the power unit.

Such design of the apparatus for current pulses action upon the central nervous system ensures administration of electro-anesthesia by the patient herself in accordance with individual reactions to pain, permits increased intensity of pulse action in case of acute pain and quicker process of electro-anesthesia.

These and other objects and advantages of the present invention will become apparent from the following detailed description of preferred embodiments thereof, taken in conjunction with the accompanying drawings, in which.

Figure 1:
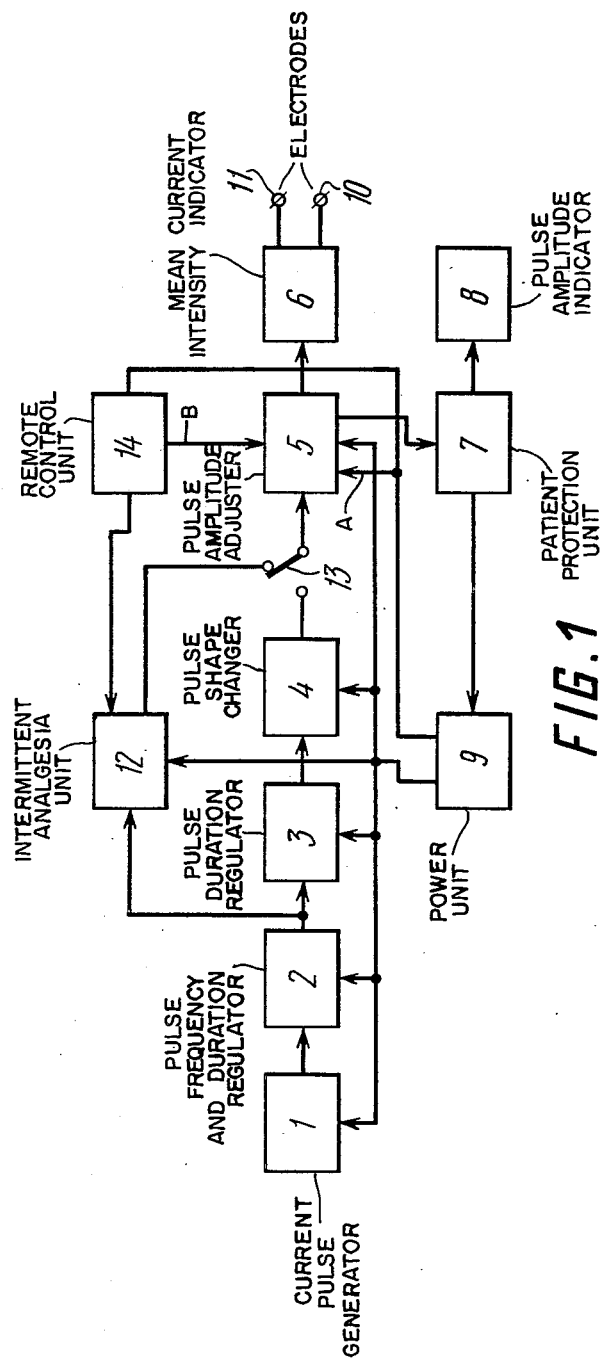
FIG. 1 is a block diagram of an apparatus for current pulses action upon the central nervous system, according to the invention.

The apparatus for current pulses action upon the central nervous system, according to the invention, comprises several series-connected units: a unit 1 (FIG. 1) for generating rhythmic current pulses for action upon the central nervous system (having the construction shown in the U.S. Pat. No. 3,989,051), a unit 2 for separate regulation of the repetition frequency and duration of current pulses, which is intended for individualization of action for each patient, when in the central nervous system of the patient the second level of the first stage of general electro-anesthesia is attained, a unit 3 for regulating the duration of current pulses, which is intended to obtain the second level of the first stage of general electro-anesthesia without any side effects in a patient (units 2 and 3 also being constructed as shown in U.S. Pat. No. 3,989,051 with unit 2 being provided for securing isolated regulation of units 1 and 3), a unit 4 for changing the shape of current pulses, which is intended to obtain the second level of the first stage of general electro-anesthesia in weak patients and children, a unit 5 for adjusting the amplitude of current pulses and a unit 6 for indicating the mean current intensity value.

The apparatus also comprises a patient protection unit 7 to prevent the amplitude of current pulses from exceeding a specific value, the input thereof being connected to another output of the unit 5 for adjusting the amplitude of current pulses, one output thereof being connected to a unit 8 for indicating the current pulses amplitude and another output being connected to a power unit 9 which is coupled to the input of the unit 1 for rhythmic current pulse action upon the central nervous system and other inputs of the units 2, 3, 4 and 5.

The output of the unit 6 for indicating the mean current intensity value is coupled to electrodes which are a bifurcated cathode 10 and a bifurcated anode 11 (shown conventionally in the drawings). The electrodes are made in a known manner as shown in U.S. Pat. No. 3,989,051.

The cathode 10 is attached to the patient's forehead area, whereas the anode is attached in the patient's neck area, below the mastoids, in order to produce in the central nervous system said second level of the first state of general electro-anesthesia.

Besides, the apparatus comprises, a delivery intermittent analgesia unit 12 (from throe to throe), which is coupled to the output of the unit 2 for separate regulation of the repetition frequency and duration of current pulses. In the illustrated embodiment of the apparatus the delivery intermittent analgesia unit 12 and the unit 4 for changing the shape of current pulses are selectively connected to the unit 5 for adjusting the amplitude of current pulses by means of a switch 13.

The apparatus also comprises, according to the invention, a unit 14 for remote control of the autoelectroanalgesia level, which the patient holds in hand, whose outputs are connected, respectively, to the intermittent analgesia unit 12, the unit 5 for adjusting the amplitude of current pulses and to the power unit 9 so that said unit 14 regulates at the outputs of said units 12, 5, 9 the repetition frequency of current pulses, their amplitude and the level of an additional direct component, respectively, according to the intensity of pain in a patient. In this case, additional inputs of the unit 5 for adjusting the amplitude of current pulses are coupled to the output of the power unit 9 and to the output of the autoelectroanalgesia level remote control unit 14 as shown by the arrows A and B in FIG. 1.

Figure 2:
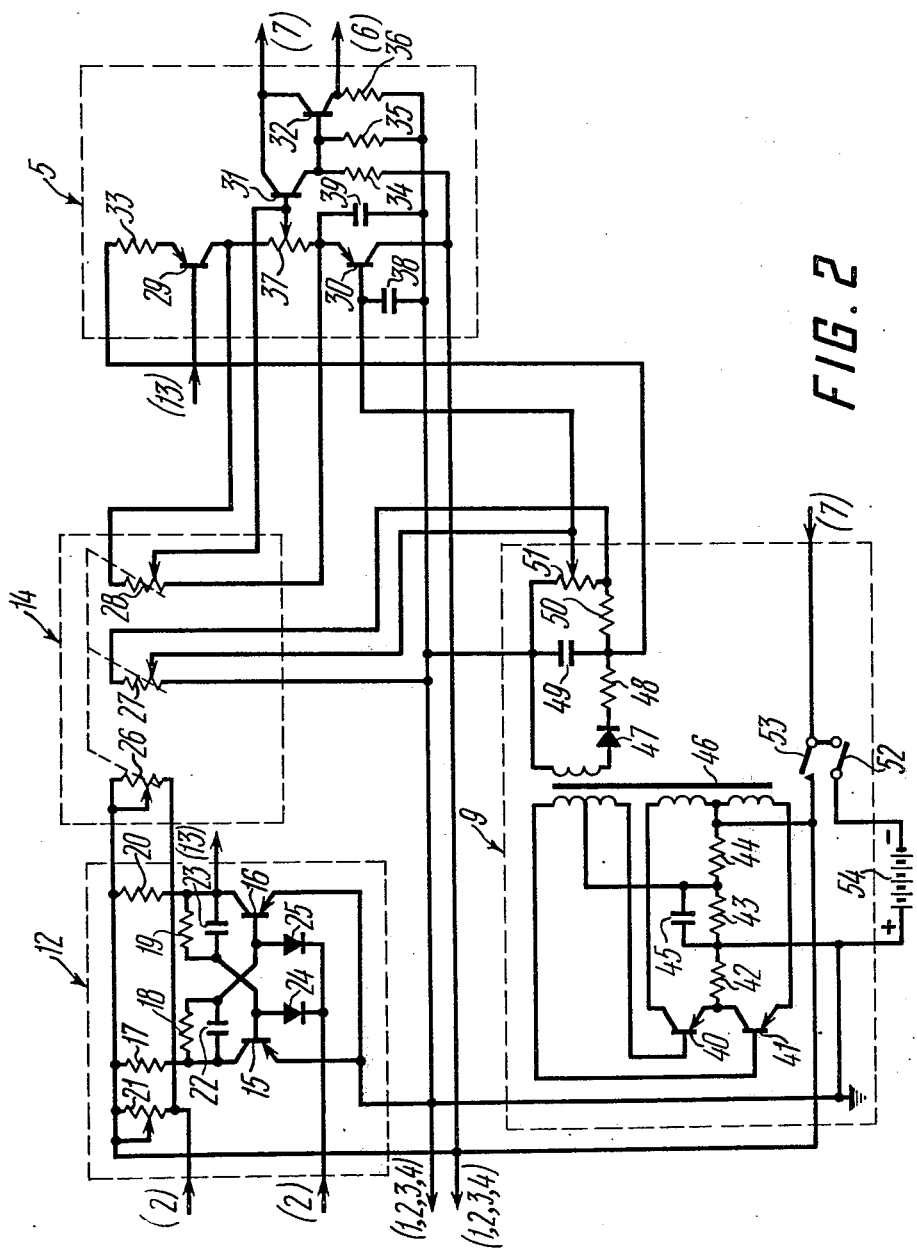
FIG. 2 is an electric circuit diagram of an intermittent analgesia unit, a unit for adjusting the amplitude of current pulses, a power unit and an autoelectroanalgesia level remote control unit of the apparatus for current pulses action upon the central nervous system, according to the invention.

FIG. 2 is an electric circuit diagram of the units 12, 14, 5 and 9. Other units of the apparatus, according to the invention, are made in a conventional manner, as shown in U.S. Pat. No. 3,989,051.

The unit 12 (FIG. 2) for intermittent analgesia is made as a counting flip-flop built around transistors 15 and 16, resistors 17, 18, 19 and 20, an adjustable resistor 21, capacitors 22 and 23 and diodes 24 and 25. The adjustable resistor 21 ensures in this unit adjustment of the pulse repetition frequency in accordance with the intensity of the patient's pain reaction. One input of the unit 12, which is the adjustable resistor 21, is coupled to an adjustable resistor 26 of the unit 14 for remote control of the autoelectroanalgesia level, whereas an output, which is the collector of the transistor 16, can be connected to the switch 13. In this case, the unit 12 is coupled by the adjustable resistor 21 and the diodes 24 and 25 to, while being coupled through the transistors 15 and 16 to an output of unit 9 the unit 2.

The autoelectroanalgesia level remote control unit 14 is made as an electromechanical regulator which comprises the above mentioned adjustable resistor 26 and adjustable resistors 27 and 28, which are, respectively, the three outputs of said unit.

The unit 5 for adjusting the amplitude of current pulses is made as a voltage generator built around transistors 29, 30, 31 and 32, resistors 33, 34, 35 and 36, an adjustable resistor 37 and capacitors 38 and 39, which permits maintaining the second level of the first stage of general electro-anesthesia irrespective of the functional state of the central nervous system of the patient.

The input of the unit 5, which is the base of the transistor 29, is connected through the switch 13 either to the unit 4 or, as shown in FIG. 2, to the output of the unit 12, whereas the outputs, the emitter and the collector of the transistor 32, are respectively connected to the inputs of the unit 6 for indicating the mean current intensity value and of the patient protection unit 7.

The output of the unit 14, which is the adjustable resistor 28, is connected to the adjustable resistor 37 which is the input of the unit 5.

The power unit 9 comprises a voltage changer, a rectifier and a regulator of the additional direct component. The voltage changer is built around transistors 40 and 41, resistors 42, 43 and 44, a capacitor 45 and a transformer 46. The rectifier comprises a diode 47, a resistor 48 and a capacitor 49. The additional direct component regulator comprises a resistor 50 and an adjustable resistor 51.

The output of the unit 14, which is the adjustable resistor 27, is connected to the adjustable resistor 51, which is the output of the power unit 9.

The power unit 9 is coupled at its outputs to the inputs of the units 1, 2, 3, 4, 5, 12 and receives an input via a switch 52 and a relay contact 53 from the patient protection unit 7. The switch 52 of the power unit 9 is to supply voltage to the changer. The relay contact 53 connected to the patient protection unit 7 serves to cut off the supply voltage produced by a power source 54 from the voltage changer, when currents in the patient circuit exceed specified values.

The apparatus for current pulses action upon the central nervous system operates, according to the invention, as follows.

The units 1, 2, 3, 4, 6, 7 and 8 (FIG. 1) operate according to the known principle of action by current pulses upon the central nervous system, as shown in U.S. Pat. No. 3,989,051.

During autoelectroanalgesia, depending on the individual reaction of the patient to pain, a sequence of pulses is formed at the output of the unit 1 and is fed via the unit 2 for separate regulation of the repetition frequency and duration of current pulses, to the delivery intermittent analgesia unit 12 and through the switch 13, when the latter is in the position shown in FIG. 1 to the input of the unit 5 for adjusting the amplitude of current pulses.

When the patient turns the knob of the electromechanical regulator of the unit 14 (FIG. 2) for remote control of the autoelectroanalgesia level, the adjustable resistors 26, 27 and 28 change simultaneously. The adjustable resistor 26 which is electrically coupled to the adjustable resistor 21 of the intermittent analgesia unit 12 increases the intensity of action by increasing the repetition frequency of pulses. The adjustable resistor 27 which is electrically connected to the adjustable resistor 51 of the power unit 9 increases the intensity of action by increasing the level of the additional direct component. The adjustable resistor 28 which is electrically connected to the adjustable resistor 37 of the unit 5 for adjusting the amplitude of current pulses increases the intensity of action by increasing the amplitude of current pulses.

Depending on the pain intensity, the patient turns the knob of the electromechanical regulator of the unit 14 and increases the pulse action, whenever pain appears.

Simultaneous increase in the amplitude, repetition frequency of pulses, accompanied by an increase in the level of the additional direct component, speeds up blockage of pain formation in the cerebral cortex.

In this manner the disclosed apparatus ensures a possibility of a quick increase in the intensity of pulse action by the patient at the moment of acute pain.

It will thus be seen that the apparatus of the invention for producing current pulse action on the central nervous system includes the pulse generating means 1 and the electrodes 10 and 11 for delivering the pulses to a patient, the several units 2–6 forming an intermediate means situated between the electrodes and the pulse generating means 1 for regulating the pulses produced thereby with respect to such factors as the frequency and duration thereof, this intermediate means including the amplitude adjusting means 5, for adjusting the amplitude of the pulses, with the apparatus also including the intermittent analgesia means 12 connected to the above intermediate means for controlling the repetition frequency of the current pulses, as well as a power means 9 for delivering power to the pulse generator means, the intermediate means, and the intermittent analgesia means, the invention providing the improvement according to which the remote control means 14 is available to the patient for controlling the autoelectroanalgesia level, this remote control means being electrically connected with the intermittent analgesia means 12, the amplitude adjusting means 5, and the power means 9 for regulating the repetition frequency of pluses controlled by the intermittent analgesia means, the amplitude of the pulses controlled by said amplitude adjusting means, and an additional direct component of the output of said power means, as by increasing the repetition of the pulses, the amplitude of the current pulses, and the level of the additional direct current component of the power means, in order to reduce pain experienced by the patient.

What is claimed is:

1. In an apparatus for providing current pulse action on the central nervous system including a current pulse generating means, electrode means for delivering the current pulses to a patient, intermediate means connected between said generating means and electrode means for regulating the current pulses with respect to factors such as the frequency and duration thereof, said intermediate means including an amplitude adjusting means for adjusting the amplitude of the current pulses, intermittent analgesia means electrically connected to said intermediate means for controlling the repetition frequency of current pulses, and power means operatively connected to said current pulse generator means, said intermediate means and said intermittent analgesia means for delivering electrical power thereto with the latter power including an additional direct component, the improvement wherein a remote control means for remote control of the autoelectroanalgesia level is available to a patient for manual control by the patient and is electrically connected with said intermittent analgesia means, said amplitude adjusting means, and said power means for regulating the latter three means to control the repetition of the pulses regulated by said intermittent analgesia means, the amplitude of current pulses regulated by said amplitude adjusting means, and the level of the additional direct component provided by said power means, as by increasing the repetition frequency of pulses, the amplitude of current pulses, and the level of the additional direct component in response to an increase of pain experienced by the patient.

2. The combination of claim 1 and wherein each of said intermittent analgesia means, amplitude adjusting means, and power means including a variable resistor for regulating the repetition frequency of said intermediate analgesia means, said amplitude of said adjusting means, and the additional direct component of said power means, and said remote control means including variable resistors respectively connected electrically to said invariable resistors of said intermittent analgesia means, amplitude adjusting means, and said power means for adjusting the latter variable resistors so as to achieve the remote regulation of pain intensity by the patient.

3. The combination of claim 2 and wherein said variable resistors of said remote control means are all interconnected for simultaneous operation by the patient.

4. The combination of claim 1 and wherein said intermediate means includes a switch means for optionally connecting said intermittent analgesia means to or for disconnecting the same from said intermediate means, so that when said switch means is in a position for disconnecting said intermittent means from said intermediate means, said remote means is still available for controlling the amplitude of the current pulses and the additional direct component provided by said power means.

* * * * *